(12) United States Patent
Nishimura et al.

(10) Patent No.: US 10,551,346 B2
(45) Date of Patent: Feb. 4, 2020

(54) ION ANALYSIS DEVICE

(71) Applicant: Hitachi High-Technologies Corporation, Minato-ku, Tokyo (JP)

(72) Inventors: Kazushige Nishimura, Tokyo (JP); Masuyuki Sugiyama, Tokyo (JP); Hideki Hasegawa, Tokyo (JP); Yuichiro Hashimoto, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 16/323,168

(22) PCT Filed: Aug. 19, 2016

(86) PCT No.: PCT/JP2016/074264
§ 371 (c)(1),
(2) Date: Feb. 4, 2019

(87) PCT Pub. No.: WO2018/034005
PCT Pub. Date: Feb. 22, 2018

(65) Prior Publication Data
US 2019/0178841 A1 Jun. 13, 2019

(51) Int. Cl.
*G01N 27/62* (2006.01)
*H01J 49/00* (2006.01)
(Continued)

(52) U.S. Cl.
CPC .......... *G01N 27/62* (2013.01); *H01J 49/0009* (2013.01); *H01J 49/044* (2013.01); *H01J 49/065* (2013.01); *H01J 49/26* (2013.01)

(58) Field of Classification Search
USPC ........................................ 250/292, 290, 281
See application file for complete search history.

(56) References Cited

U.S. PATENT DOCUMENTS

2003/0155497 A1    8/2003  Kato
2004/0063113 A1*   4/2004  Agnes ............... H01J 49/04
                                                       435/6.12
(Continued)

FOREIGN PATENT DOCUMENTS

JP    2012-28336 A   2/2012
JP    5552671 B2     7/2014
(Continued)

OTHER PUBLICATIONS

International Search Report (PCT/ISA/210) issued in PCT Application No. PCT/JP2016/074264 dated Nov. 15, 2016 with English translation (three (3) pages).
(Continued)

*Primary Examiner* — Kiet T Nguyen
(74) *Attorney, Agent, or Firm* — Crowell & Moring LLP

(57) ABSTRACT

An ion analysis device includes: an ion source that ionizes an analyte in a liquid sample; an ion guide into which droplets and ions produced in the ion source are introduced, the ion guide having different outlets, one outlet being an ion outlet for the ions and the other outlet being a droplet outlet for the droplets; an ion analysis unit that analyzes ions ejected from the ion outlet; a droplet measurement unit that is placed on an axis of the droplet outlet, and measures the amount of droplets; and an analysis control section that compares the amount of droplets measured at the droplet measurement unit with a threshold.

13 Claims, 10 Drawing Sheets

(51) Int. Cl.
*H01J 49/04* (2006.01)
*H01J 49/06* (2006.01)
*H01J 49/26* (2006.01)

(56) References Cited

U.S. PATENT DOCUMENTS

2011/0049357 A1   3/2011   Giles
2015/0206731 A1   7/2015   Zhang et al.

FOREIGN PATENT DOCUMENTS

JP    2015-521784 A    7/2015
WO    WO 03/065406 A1   8/2003

OTHER PUBLICATIONS

Japanese-language Written Opinion (PCT/ISA/237) issued in PCT Application No. PCT/JP2016/074264 dated Nov. 15, 2016 (three (3) pages).

* cited by examiner

ION ANALYSIS DEVICE

TECHNICAL FIELD

The present invention relates to an ion analysis device, or an ion analyzer.

BACKGROUND ART

Ion analysis devices such as mass spectrometers and the like are utilized to perform component analyses on a biological sample such as blood, urine and the like. In a typical example, a biological sample is analyzed through pretreatment process, separation process using LC (Liquid Chromatograph), and mass spectrometry process in this order. In the pretreatment process, deproteinization of the biological sample, concentration of an analyte and the like are performed. In the separation process using LC, an analyte is separated from other substances by use of a difference in interaction with column. In LC, water and/or an organic solvent such as methanol and/or the like are used, and solvent composition is chosen to be suitable for separation of an analyte. According to the conditions of solvent composition, the rate of solvent flow, a column type, a column temperature and/or the like, an analyte passes through LC within a unique retention time, which is then introduced into the mass spectrometer. In the mass spectrometry process, an analyte is ionized under atmospheric pressures, and analyte ions are introduced into a vacuum, and then are separated and detected according to the mass-to-charge ratio m/z. The analytes are classified based on the measured retention time and the mass-to-charge ratio m/z, and the analytes are quantitated based on measured signal strength.

For ionization techniques used for a liquid sample using an ion source of an ion analysis device, a technique of using an atomizer to atomize and spray liquid is used. In Electrospray ionization (ESI), a liquid sample is passed through a small tube and high voltage is applied to an outlet of the small tube. The liquid sample is electrically charged at the high voltage, so that the liquid sample at the outlet of the small tube is atomized in a mist form due to electric repulsion to produce charged droplets. In ESI, a nebulizer gas and a heated gas flow coaxially with the liquid sample. The nebulizer gas allows the liquid sample to be stably sprayed. The solvent in the sprayed charged droplets is volatilized, so that the analyte in the droplets is ionized. The heated gas accelerates vaporization of the solvent. The vaporization efficiency depends on the solvent composition and the flow rate of the liquid sample. Therefore, under the condition that water makes up a high percentage in the composition or the condition that the flow rate is high, the vaporization efficiency is decreased and thus the ionic strength is reduced as compared with the amount of charged droplets. The vaporization efficiency of the solvent is also decreased by a matrix-derived component of the sample such as blood, urine or the like and thus the ionic strength is reduced. In the case of low vaporization efficiency and a large amount of charged droplets, the vaporization can be accelerated by increasing the temperature and/or the flow rate of the heated gas. On the other hand, excessive heating brings the liquid sample to a boil, causing an unstable ionic strength. Because of this, there is a need to select heated-gas conditions appropriate for the solvent composition and the flow rate.

In addition to ESI, the ionization techniques employed include APCI (Atmospheric Pressure Chemical Ionization, APPI (Atmospheric Pressure Photoionization), and the like. In APCI, after a liquid sample is atomized with a nebulizer gas and the solvent is volatilized with a heated gas, the sample is ionized with a corona discharge. In APPI, a liquid sample is atomized, which is then irradiated with light to be ionized. Similarly to ESI, there is a need in APCI and APPI for selection of heated-gas conditions appropriate for the solvent composition and the flow rate. APCI and APPI, however, differ from ESI in that high voltage is not applied at a small-tube's outlet. Because of this, in APCI and APPI, the droplets are electrically neutral.

Patent Literature 1 describes an ion guide having an outlet for ions and an outlet for airflow. In the ion guide, an ion transport mechanism transports ions from an ion source under atmospheric pressures to a mass spectrometer under a high vacuum, and the ion transport mechanism is used to transport ions by an electric field under pressure ranging from several tens to several thousands of Pa. The ions produced by the ion source pass, together with ambient gas, through a vacuum chamber entrance to enter the ion guide because of a pressure difference between the ion source and the ion guide. The airflow containing the ions is adiabatically expanded to be accelerated to hypersonic speeds, and travels in straight line within the ion guide. In Patent Literature 1, two ion guides with different central axes are connected. Low-mass ions are guided by an electric field and are separated from the airflow, which are then ejected from the ion guide having the central axis different from the ion's entry axis, to be transported into the mass spectrometer. The charged droplets, which have high mass, are not separated from the airflow and, together with the airflow, are ejected from the outlet different from one for the ions. Electrically neutral droplets are insensitive to the electric field, and therefore those droplets, together with the airflow, are also ejected from the outlet different from one for ions.

Patent Literature 2 describes an ion guide having an ion outlet placed out of the ion's entry axis for separation between the charged droplets and the ions. The high-mass droplets travel together with the airflow in straight lines, and only the low-mass ions are transported to the outlet of the ion guide by an electric field, and then transported into the mass spectrometer.

CITATION LIST

Patent Literature

Patent Literature 1: Japanese Patent No. 5552671
Patent Literature 2: Japanese Unexamined Patent Application Publication (Translation of PCT Application) No. 2015-521784

SUMMARY OF INVENTION

Technical Problem

Typically, the LC separation takes about 10 minutes. Because the sample detection time is short such as several seconds, searching for LC conditions such as solvent composition, a flow rate and the like needs to perform sample measurements several times in order to adjust the temperature and the flow rate of the heated gas so as to be adapted to the conditions. Therefore, it takes time to adjust the apparatus conditions such as a flow rate of the heated gas and the like. Further, in the conventional art, when the amount of droplets is increased by a change in solvent composition of LC or by a matrix influence on the sample, the conditions for the ion source cannot be set appropriately, and the apparatus may be contaminated by impurities in the droplets.

The droplets sprayed at the ion source contain impurities as well as the analyte, and if the non-vaporized droplets are introduced into the vacuum of the apparatus, the impurities are deposited to contaminate the vacuum chamber. In particular, the entrance of the vacuum chamber near the ion source is easily contaminated. Impingement of ions onto the contaminated portion causes electrification, which in turn causes repulsion of the ions and/or charged droplets introduced into the vacuum chamber, resulting in a reduction in sensitivity. For the mass spectrometer, calibrator samples are measured at regular intervals (the order of once per day) in order to check whether contaminations cause a reduction in sensitivity. When the sensitivity of the calibrator sample is below a threshold value, the ion source and/or the vacuum chamber is disassembled and cleaned to remove the contaminations. After removal of the contaminations, the calibrator sample is measured to check restoration of sensitivity.

The droplets or charged droplets produced at the ion source in this manner are used as an important indicator of apparatus states such as ionization efficiency, contamination and the like. However, in the method of measuring calibrator samples, the sensitivity check is performed only once a day prior to the start of measurement, and therefore if a reduction in sensitivity is caused by contamination during the measurement of biological samples, this makes impossible to detect an analyte with high accuracy. Further, since a warning that the sensitivity is reduced to be below a predetermined sensitivity cannot be given during the measurement of biological samples, the samples measured after the reduction in sensitivity are required to be remeasured, resulting in wastes of samples and measurement time. An increase of the frequency of measurements of the calibrator samples causes increases of the measurement time and the running costs.

In the apparatus described in Patent Literatures 1 and 2, it takes time to adjust the apparatus conditions when the LC separation conditions appropriate for an analyte are searched for. Further, the apparatus conditions cannot be adjusted when the ionic strength of the analyte is low and the amount of droplets is large, so that the apparatus may be contaminated by impurities in the droplets, and this may possibly lead to a reduction in sensitivity. If there is contamination of the mass spectrometer, the contaminated site is electrically charged, and in turn repulsion of the analyte ions and the charged droplets causes reductions in both strengths.

Solution to Problem

An ion analysis device according to the present invention includes: an ion source that ionizes an analyte in a liquid sample; an ion guide into which droplets and ions produced in the ion source are introduced, the ion guide having different outlets, one outlet being an ion outlet for the ions and the other outlet being a droplet outlet for the droplets; an ion analysis unit that analyzes ions ejected from the ion outlet; a droplet measurement unit that is placed on an axis of the droplet outlet, and measures the amount of droplets; and an analysis control section that compares the amount of droplets measured at the droplet measurement unit with a threshold.

Advantageous Effects of Invention

According to the present invention, a reduction in adjustment time for apparatus conditions or a reduction in contamination can be achieved.

The above and other problems, configurations and advantages will be more apparent from the following description of embodiments.

DESCRIPTION OF EMBODIMENTS

Embodiments according to the present invention will now be described with reference to the accompanying drawings.

First Embodiment

Figure 1:
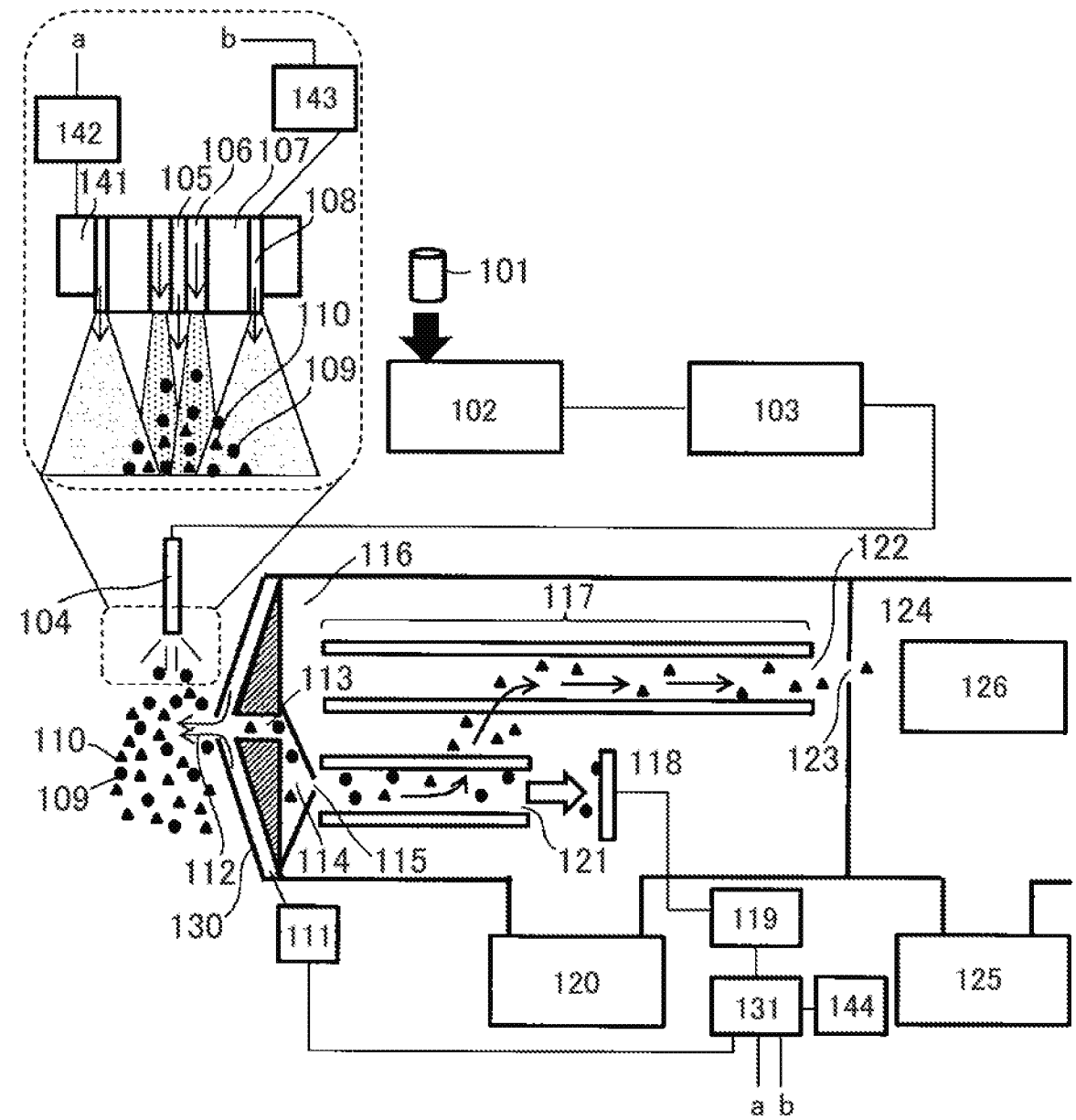
FIG. 1 is a schematic diagram illustrating example configuration of an ion analysis device.

Described in the embodiment is the configuration that monitors charged droplets which have been produced at an ion source, in order to reduce the contamination in the apparatus and warns the user of a reduction in sensitivity accompanied by the contamination. FIG. 1 is a schematic diagram illustrating example configuration of an ion analysis device in accordance with the embodiment. The ion analysis device illustrated in FIG. 1 has a sample pretreatment device 102, a liquid chromatograph device (LC) 103, and a mass spectrometer. The ion analysis device also includes an ESI spray 104 as an ion source.

At the sample pretreatment device 102, a liquid sample 101 such as urine, blood or the like is subjected to deproteinization, analyte separation and purification, analyte concentration, and the like. The sample after the process is introduced into the LC 103. The analyte is separated by an interaction difference between a mobile phase and a stationary phase in the LC, and passes through the LC for a substance-specific retention time. The analyte which has passed through the LC is ionized at the ESI spray 104 placed under atmospheric pressures.

Enlarged section of the leading end of the ESI spray 104 is schematically illustrated in a portion enclosed with a broken line. In the ESI spray 104, three fluids, i.e. a liquid sample, nebulizer gas and heated gas, flow coaxially. A voltage from about 1 kV to about 10 kV is applied to a center liquid-sample flow path 105 so that the liquid is electrically charged. The liquid thus charged at the leading end of the flow path 105 undergoes electrostatic repulsion, and thus is atomized to produce charged droplets 109. The nebulizer gas flows in a flow path 106 placed on the outside of the liquid-sample flow path 105. The nebulizer gas aids in the atomization of the charged droplets to provide stable spraying of the ESI spray. A flow path 108 is placed on the outside of the nebulizer-gas flow path 106, and a heater 141 is mounted around the flow path 108 in order to heat the gas within the flow path 108. The flow rate of the heated gas is adjusted by a flow-rate control section 143 and the temperature of the heated gas is adjusted by a temperature control section 142. The heated gas volatilizes the solvent in the charged droplets 109 to produce analyte ions 110. If the heated gas heats the liquid-sample flow path 105, the liquid sample comes to a boil, and thus the ionic strength varies. To address this, a void space 107 is provided for thermal insulation between the heated-gas flow path 108 and, the liquid-sample flow path 105 and nebulizer-gas flow path 106.

The charged droplets 109 contain impurities in addition to the analyte. The impurities may contaminate the ion source and/or the vacuum in the mass spectrometer and/or cause an increase in detector noise, leading to a reduction in apparatus sensitivity. In particular, an ion inlet 113 and/or an intermediate pressure chamber 114 of the mass spectrometer which is located near the ion source are easily contaminated. Impingement of the charged droplets 109 and the ions 110 onto the contaminated portion causes electrification, which in turn causes repulsion of the charged droplets 109 and the ions 110, resulting in a reduction in the amounts of charged droplets 109 and ions 110 which will be introduced downstream. A higher temperature of the heated gas is recommended to volatilize the solvent in the charged droplets 109 for the purpose of preventing a reduction in sensitivity. On the other hand, there are constraints regarding thermal decomposition of the analyte by the heating, heat transfer to the liquid-sample flow path 105 to boil the liquid sample resulting in unstable ionic strength, or the like.

The analyte ions 110 produced at the ion source, and the non-desolvated, residual charged droplets 109 are sucked into the ion inlet 113 by an electric field applied to a counter plate electrode 130 and a pressure difference between the ion source and a first differential pumping chamber 116. In the ion inlet 113, a flow of a counter gas 112 is directed toward the ion source chamber from a gas feeding control section 111, i.e., directed outward from the ion inlet 113. The charged droplets 109 susceptible to airflow because of large particle size are pushed back to the ion source chamber by the counter gas 112 in order to reduce the entry of charged droplets 109 into the vacuum.

The ions 110 and the charged droplets 109, which have passed through the ion inlet 113, are introduced into an intermediate pressure chamber 114. The intermediate pressure chamber 114 is a space provided between the ion inlet 113 and the first differential pumping chamber 116, in which the pressure ranges from 1000 Pa to several tens of thousands Pa. The central axes of the ion inlet 113 and a pore 115 are offset from each other in order to allow the charged droplets 109 to impinge on a wall face of the intermediate pressure chamber 114 for a reduction in intrusion of the charged droplets into the first differential pumping chamber 116.

The pressure in the first differential pumping chamber 116 is maintained at from 100 Pa to several thousands Pa by a vacuum pump 120. An ion guide 117 is placed in the first differential pumping chamber 116. The charged droplets 109 are removed by the ion guide 117 and the ions 110 are guided into an ion analysis chamber 124 located further downstream. The airflow entering the first differential pumping chamber 116 is adiabatically expanded by a pressure difference between the ion source chamber and the first differential pumping chamber 116, and therefore is accelerated to hypersonic speeds and Mach disk is formed. The charged droplets 109 and the ions 110, together with the airflow, are accelerated to hypersonic speeds and travel in straight lines within the ion guide 117.

Figure 2:
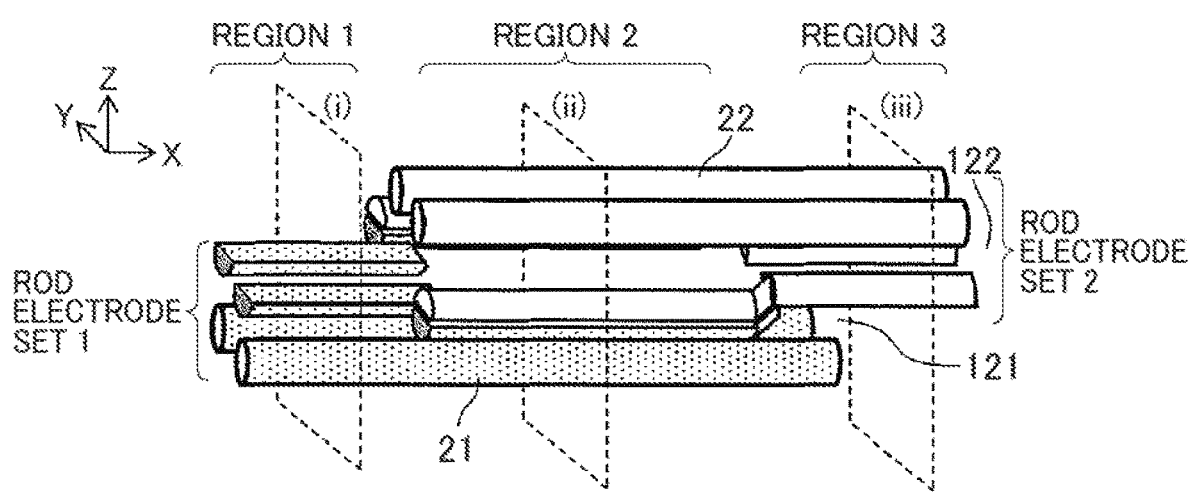
FIG. 2 is a perspective schematic view illustrating an example ion guide.
Figure 3:
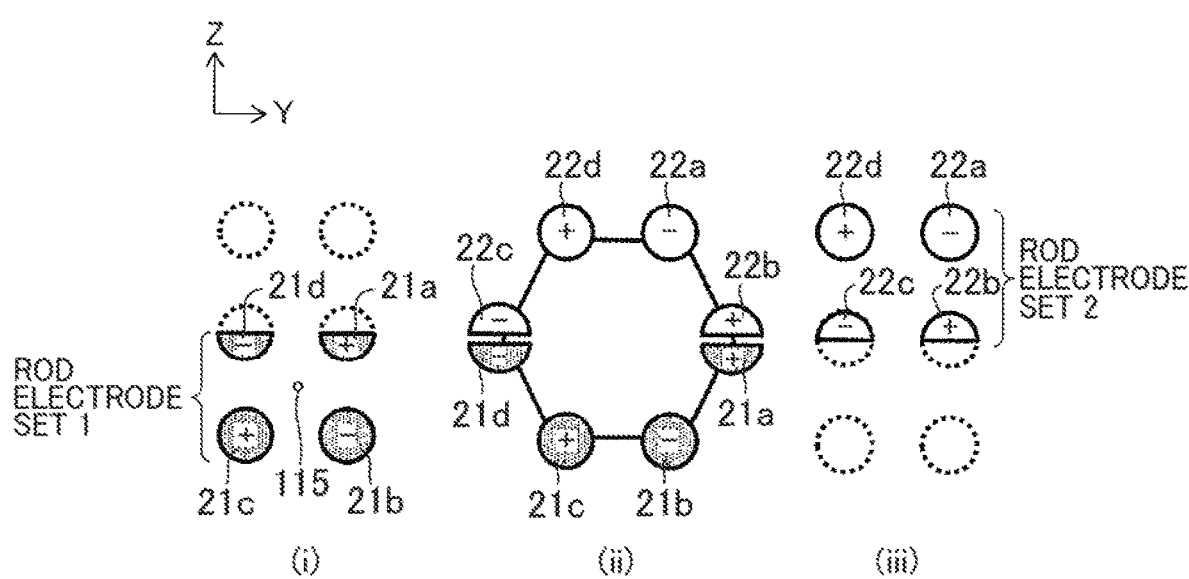
FIG. 3 is a schematic diagram of cross-section in a radial direction (YZ plane) of the ion guide.

FIG. 2 and FIG. 3 are schematic diagrams illustrating example configuration of the ion guide. FIG. 2 is a perspective schematic view illustrating the entire ion guide. FIG. 3 shows schematic diagrams of cross-section in a radial direction (YZ plane) in positions shown with (i), (ii), (iii) in FIG. 2.

A set of rod electrodes 21 located on the side of the incoming ions and charged droplets is defined as a rod electrode set 1, and a set of rod electrodes 22 located on the side of the outgoing ions is defined as a rod electrode set 2. In the example, the rod electrode set 1 is made up of four rod electrodes 21a, 21b, 21c, 21d, and the rod electrode set 2 is made up of four rod electrodes 22a, 22b, 22c, 22d. The rod electrodes 21d, 22c, 21a, 22b are each formed in a semicircular column shape or the like such that the paired rod electrodes 21d, 22c form a shape close to a single circular column or polygonal column and likewise the paired rod electrodes 21a, 22b form a shape close to a single circular column or polygonal column. The center axis of the rod electrode set 1 and the center axis of the rod electrode set 2 are parallel to each other, but are offset by a certain distance from each other in the Z-axis direction. Also, the rod electrode set 1 and the rod electrode set 2 overlap each other in a partial region in the longitudinal direction. And, in the overlapping region, as illustrated in FIG. 3, the rod electrodes of the rod electrode set 1 and the rod electrode set 2 are combined with each other to form a single multipolar ion guide.

Reference symbols "+", "−" in FIG. 3 refer to phases of RF voltage applied from the ion guide power supply to the rod electrodes. The RF voltages equal in phase, in amplitude and in frequency are applied to the rod electrodes marked with the same symbol. The RF voltage is applied such that, in the same rod electrode set, opposing rod electrodes are in a same phase and adjacent rod electrodes are in opposite phases. Also, the RF voltages equal in phase, in amplitude, in frequency are applied to the adjacent rod electrodes 21d, 22c from different rod electrode sets and the adjacent rod electrodes 21a, 22b from different rod electrode sets. Further, a DC offset voltage as well as the RF voltage is applied to the rod electrode sets. The same offset DC voltage is applied to the rod electrodes included in the same rod electrode set. The offset DC voltage is applied in such a manner as to create an electric field that moves the ions of the measured sample from the rod electrode set 1 toward the rod electrode set 2.

As illustrated in FIG. 2, the ion guide is divided into three regions, regions 1 to 3. The positional relationship in the radial direction (YZ plane) between the sets of rod electrodes 21, 22 varies in each region, and therefore the resulting pseudopotential also varies. The pseudopotential is potential that exerts to the ions a force as time average when an electric field changing at a speed at which ion motion cannot follow is applied.

In the region 1, the four rod electrodes of the rod electrode set 1 are placed in positions close to the apexes of an approximate square, so that a quadrupole ion guide is formed. By the RF voltage applied to the four rod electrodes of the rode electrode set 1, a pseudopotential well in the radial direction (YZ plane) is created. In the region 1, because pseudopotential barrier exists between the rod electrode set 1 and the rod electrode set 2, the ions are not able to move between the rod electrode sets.

In the region 2, the rod electrode set 1 and the rod electrode set 2 overlap each other. Also, the distance between the set of rod electrodes 21a, 22b and the set of rod electrodes 21d, 22c increases as compared with the positions in the region 1 and the region 3. Thus, as illustrated in FIG. 3, a hexapole ion guide is formed in which the set of rod electrodes 21a, 22b, the rod electrode 21b, the rod electrode 21c, the set of rod electrodes 21d, 22c, the rod electrode 22d and the rod electrode 22a are placed in positions corresponding to the apexes of an approximate regular hexagon. Because the RF voltage equal in phase, amplitude and frequency is applied to the set of rod electrodes 21d, 22c and the set of rod electrodes 21a, 22b, respectively, the set of rod electrodes 21d, 22c and the set of rod electrodes 21a, 22b can respectively be considered as respective single poles in terms of pseudopotential.

The rod electrode set 1 and the rod electrode set 2 are combined to form a hexapole, whereby a single pseudopotential well having a minimum near the center of a range surrounded with the rods is created. No pseudopotential barrier exists between the rod electrode set 1 and the rod electrode set 2, and therefore ions can freely move between the rod electrode set 1 and the rod electrode set 2. On the other hand, DC potential in the radial direction (YZ plane) is created by a difference between the offset DC voltages applied to the rod electrode set 1 and the rod electrode set 2. The DC potential exerts a force that moves low mass ions in the Z direction (direction from the rod electrode set 1 toward the rod electrode set 2). On the other hand, the high mass charged droplets 109 are insusceptible to an electric field and travel together with the airflow in straight lines. Because of this, the ions 110 and the charged drops 109 are separated from each other, and then the separated charged droplets 109 pass through a charged-droplet outlet 121 of the ion guide 117, and then exit the ion guide.

In the region 3, the distance between the set of rod electrodes 21a, 22b and the set of rod electrodes 21d, 22c decreases as compared with the positions in the region 2, and the four rod electrodes of the rod electrode set 2 are placed in positions close to the apexes of an approximate square. Similarly to the region 1, by the four rode electrodes of the rod electrode set 2, a pseudopotential well is created, so that the ions are focused on the center axis of the rod electrode set 2 in the region 3. The focused ions 110 are ejected from an ion outlet 122 of the ion guide 117, and then pass through a pore 123 to be introduced into the ion analysis chamber 124.

It should be noted that a portion corresponding to the region 1 may be removed from the ion guide in the example, and the airflow containing the ions and charged droplets after passing through the pore 115 may be caused to enter a range surrounded with the rod electrodes 21a, 21b, 21c, 21d of the rod electrode set 1 in the region 2, while being parallel to the center axis of the region 2 of the ion guide.

Figure 4:
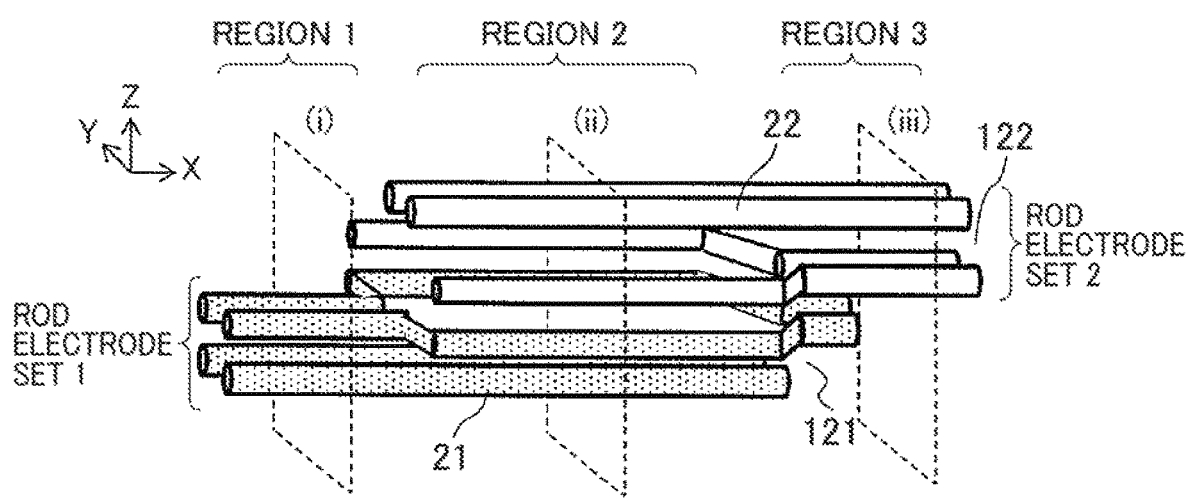
FIG. 4 is a perspective schematic view illustrating an example ion guide.
Figure 5:
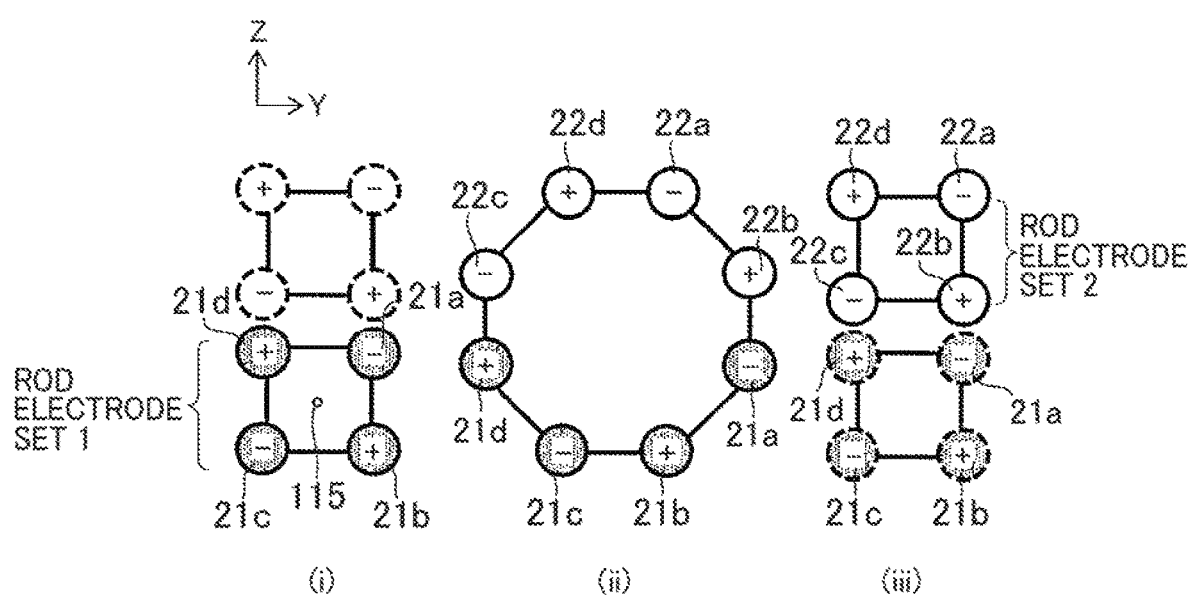
FIG. 5 is a schematic diagram of cross-section in a radial direction (YZ plane) of the ion guide.

FIG. 4 and FIG. 5 are schematic diagrams illustrating another example configuration of the ion guide. FIG. 4 is a perspective schematic view illustrating the entire ion guide. FIG. 5 shows schematic diagrams of cross-section in a radial direction (YZ plane) in positions shown with (i), (ii), (iii) in FIG. 4.

A set of rod electrodes 21 located on the side of the incoming ions and charged droplets is defined as a rod electrode set 1, and a set of rod electrodes 22 located on the side of the outgoing ions is defined as a rod electrode set 2. As in the case of the ion guide described in FIG. 2 and FIG. 3, the center axis of the rod electrode set 1 and the center axis of the rod electrode set 2 are parallel to each other, but are offset by a certain distance from each other in the Z-axis direction. Also, the rod electrode set 1 and the rod electrode set 2 overlap each other in a partial region in the longitudinal direction. And, in the overlapping region, as illustrated in FIG. 5, the rod electrodes of the rod electrode set 1 and the rod electrode set 2 are combined with each other to form a single multipolar ion guide. The same offset DC voltage is applied to the rode electrodes included in the same rod electrode set. Reference symbols "+", "−" in FIG. 5 refer to phases of RF voltage, and the RF voltages equal in phase, in amplitude, in frequency are applied to the rod electrodes marked with the same symbol.

In the region 1, a quadrupole ion guide is formed by the four rod electrodes 21a, 21b, 21c, 21d of the rod electrode set 1. In the region 2, the distance between the rod electrodes 21a, 21d of the rod electrode set 1 and the rod electrodes 22b, 22c of the rod electrode set 2 increases as compared with the positions in the region 1, so that the rod electrodes are located respectively in positions corresponding to the apexes of an approximate regular octagon as illustrated in FIG. 5. The rod electrode set 1 and the rod electrode set 2 are combined to form an octopole, whereby a single pseudopotential well having a minimum near the center of a range surrounded with the rods is created. No pseudopotential barrier exists between the rod electrode set 1 and the rod electrode set 2, and therefore ions can freely move between the rod electrode set 1 and the rod electrode set 2. If an offset DC voltage is applied in such a manner as to create an electric field that moves the ions of measured sample from the rod electrode set 1 toward the rod electrode set 2, the ion can be separated from the charged droplets to move from the rod electrode set 1 toward the rod electrode set 2 in the region 2. On the other hand, the high mass charged droplets 109 are insusceptible to an electric field and travel together with the airflow in straight lines. Because of this, the ions 110 and the charged drops 109 are separated from each other, and then the separated charged droplets 109 pass through the charged-droplet outlet 121 of the ion guide 117, and then exit the ion guide.

The ions that have moved toward the rod electrode set 2 are introduced into the region 3. In the region 3, a quadrupole ion guide is formed by the four rod electrodes 22a, 22b, 22c, 22d of the rod electrode set 2, and the ions are focused on the center axis of the quadrupole ion guide. The focused ions 110 are ejected from the ion outlet 122 of the ion guide 117, and then pass through the pore 123 to be introduced into the ion analysis chamber 124.

The octopole has been described here as an example, but any multipole higher than the octopole, such as decapole, dodecapole, hexadecapole, icosapole or the like, may be used. It should be noted that a portion corresponding to the region 1 may be removed from the ion guide, and the airflow containing the ions and charged droplets after passing through the pore 115 may be caused to enter a range surrounded with the rod electrodes 21a, 21b, 21c, 21d of the rod electrode set 1 in the region 2, while being parallel to the center axis of the region 2 of the ion guide. The ion guide 117 schematically illustrated in FIG. 1 is illustrated as an aspect in which the region 1 is removed.

The pseudopotential well formed by the quadrupole has great influence for focusing ions on the axis because the potential gradient around the minimum is greater than that in a higher-order multipole or a ring-stack ion guide. The greater the influence for focusing ions, the higher the efficiency of allowing ions to pass through the pore 123 at the subsequent stage of the ion guide, and high-sensitivity measurement is enabled.

Referring back to FIG. 1, after the charged droplets 109 has passed through the charged-droplet outlet 121 of the ion guide 117, the charged droplets 109 impinge on an electrode 118 connected to an ammeter 119. The electrode 118 placed on the axis of the charge-droplet outlet 121 and the ammeter 119 connected to the electrode 118 form a droplet measurement unit which measures a current value of the charged droplets 109 impinging on the electrode 118 in order to monitor the amount of charged droplets 109. The measured current value is transmitted to an analysis control section 131. The analysis control section 131 actuates, as a function of the current value, the temperature control section 142, the flow-rate control section 143 and the gas feeding control section 111 to change the temperature of the ion source (i.e., the temperature of the heater 141), the flow rate of heated gas to be passed through the ESI spray 104, and the flow rate of counter gas 112. The analysis control section 131 also displays a warning of the need for user maintenance on a display unit 144, and performs processes such as discontinuing of sample measurement, suspension of the subsequent sample measurement, and the like.

If the ion inlet 113 and/or the intermediate pressure chamber 114 are contaminated, then the contaminated portion is electrically charged to cause a reduction in strength of both the charged droplets 109 and the ions 110. Because of this, a reduction in apparatus sensitivity can be monitored by measuring the charged droplets 109. In the embodiment, the amount of charged droplets is measured alongside the analyte ion strength during the sample measurement, so the reduction in sensitivity can be monitored during the sample measurement. Because of this, the frequency of requiring continuously repeated measurements on the sample while the sensitivity is reduced can be decreased, leading to reductions in consumables and measurement time loss. Further, the frequency of measuring the calibrator samples can be decreased, leading to a reduction in running costs.

The ion guide 117 used in the embodiment is desirably configured to employ the aforementioned multipole rod electrode in terms of high ionic permeability efficiency, but any other shape may be employed as long as it has the charged-droplet outlet 121 and the ion outlet 122. For example, an ion guide of stacked ring structure as described in Patent Literature 1 may be used.

The pressure in the ion analysis chamber 124 is maintained at or below 0.1 Pa by a vacuum pump 125. In the ion analysis chamber 124, a mass analysis unit, a detector, and the like are placed to form an ion analysis unit 126, in which the ions 110 are separated and detected according to the mass-to-charge ratio m/z. Mass spectrometry methods include Quadrupole filter mass analyzer, Triple quadrupole filter mass analyzer, Ion trap mass analyzer, Time of flight mass analyzer, Fourier transform mass analyzer, and the like. Any other mass analyzer other than above may be used. Further, instead of the mass analyzer, Ion mobility spectrometer, Differential mobility spectrometer, and the like may be used. Any other measurement instrument to detect ions may be used.

Figure 6:
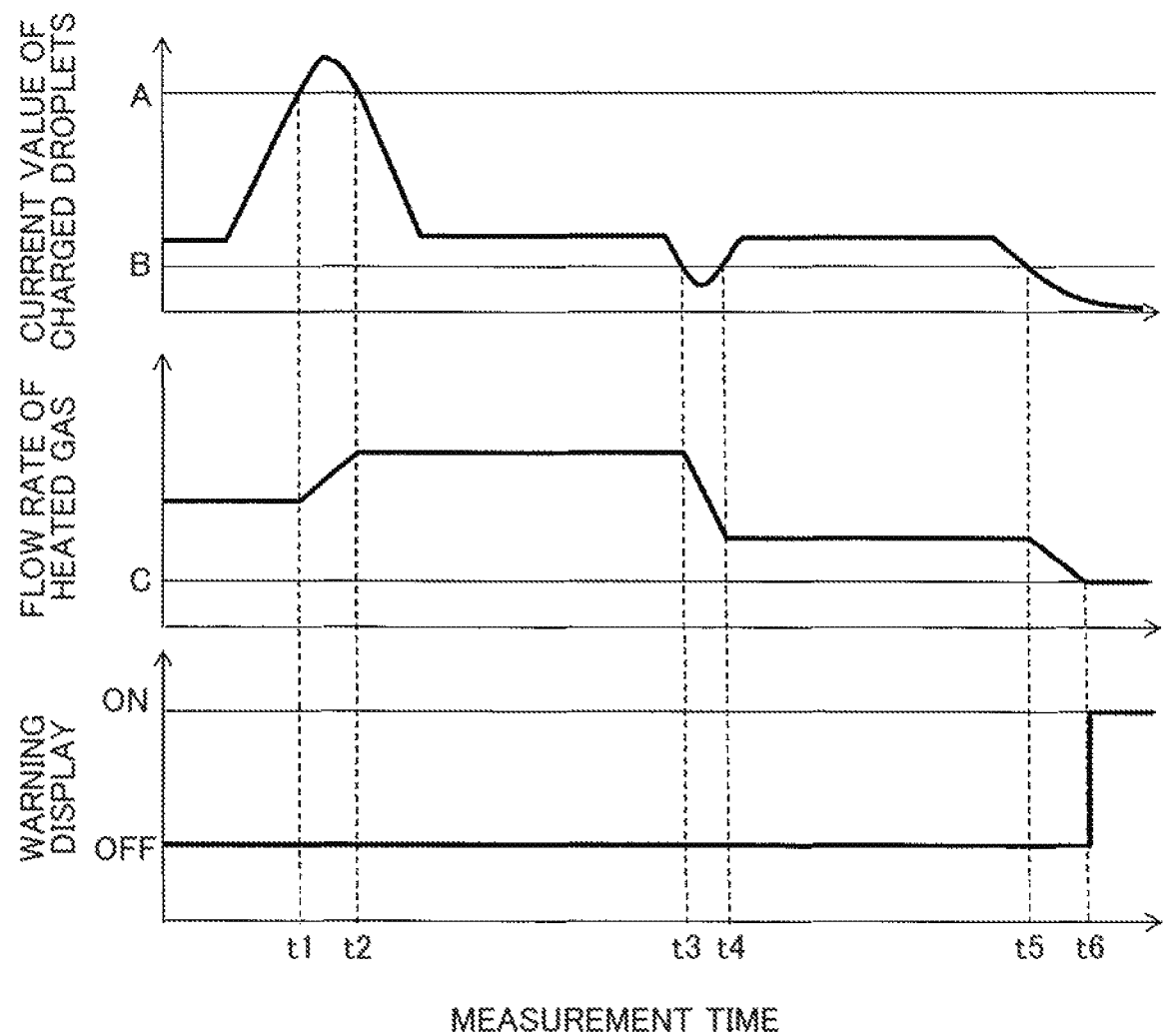
FIG. 6 is a diagram illustrating an example control sequence to control apparatus parameters.

FIG. 6 is a diagram illustrating an example control sequence to control apparatus parameters based on the measured amount of charged droplets. This is an example of using a current value of the charged droplets to control the flow rate of heated gas and warning display. Threshold A is an upper limit of the electric current of charged droplets, threshold B is a lower limit of the electric current, and threshold C is a lower limit of the flow rate of heated gas to be passed through the ESI spray.

In the initial state, the current value of the charged droplets is between the upper limit A and the lower limit B, which is within a proper range. With the influences of a change in LC solvent composition and of sample-derived impurities, if the components of the charged droplets vary so that the charged droplets become resistant to volatilization, the current value measured by the ammeter 119 increases. At time t1, the current value exceeded the upper limit A. The charged droplets contain sample-derived impurities, and thus the ion inlet 113 and the intermediate pressure chamber 114 are contaminated. For contamination prevention, upon the current value of the discharge droplets exceeding the upper limit A, the analysis control section 131 instructs the flow-rate control section 143 to increase the flow rate of heated gas to be passed through the ESI spray in order to reduce the charged droplets to lower the current value. At time 2, upon the current value falling below the upper limit A, the analysis control section 131 instructs the flow-rate control section 143 to stop increasing the flow rate of heated gas.

If the components of the charged droplets vary so that the droplets are easily volatilized, or if the apparatus sensitivity is reduced by contaminations, the amount of charged droplets decreases to lower the current value. At time t3, upon the current value falling below the lower limit B, the analysis control section 131 instructs the flow-rate control section 143 to decrease the flow rate of heated gas. Where the flow rate of heated gas decreases and the current value increases, it is determined that the decrease in current value is attributed to variations in component of the charged droplets for easier volatilization. At time t4, upon the current value exceeding the lower limit B, the analysis control section 131 instructs to stop decreasing the flow rate of heated gas.

Likewise, at time t5, upon the current value falling below the lower limit B, the analysis control section 131 decreases the flow rate of heated gas. At time t6, even after the flow rate of heated gas has reached the lower limit C, the current value remains below the lower limit B. Therefore, the analysis control section 131 determines that the decrease of the current value is caused by contamination, and displays a warning on the display unit 144 to notify the user of the need of maintenance. It is noted that, in this example, only a reduction of the amount of charged droplets measured by the droplet measurement unit is used as an indicator to determine if the apparatus is contaminated, but both the amount of charged droplets and the ionic strength detected by the ion analysis unit 126 may be used to determine if the apparatus is contaminated. If the apparatus is contaminated, the ionic strength of the analyte detected by the ion analysis unit is reduced together with the amount of charged droplets.

In FIG. 6, the flow rate of heated gas is controlled as an apparatus parameter. Alternatively, by controlling the flow rate of counter gas, the temperature of the heated gas, and/or the like, the same advantageous effects can be produced. If the flow rate of counter gas is increased, the charged droplets 109 are pushed back toward the side opposite to the ion inlet 113. Because of this, the amount of charged droplets entering the ion inlet 113 can be reduced for a reduction in contamination in the apparatus. Further, if the temperature of the heated gas is increased, the volatilization of the charged droplets 109 is accelerated, resulting in a decrease in charged droplets.

Second Embodiment

In the embodiment, a method of measuring droplets other than the electric current measurement will be illustrated.

Figure 7:
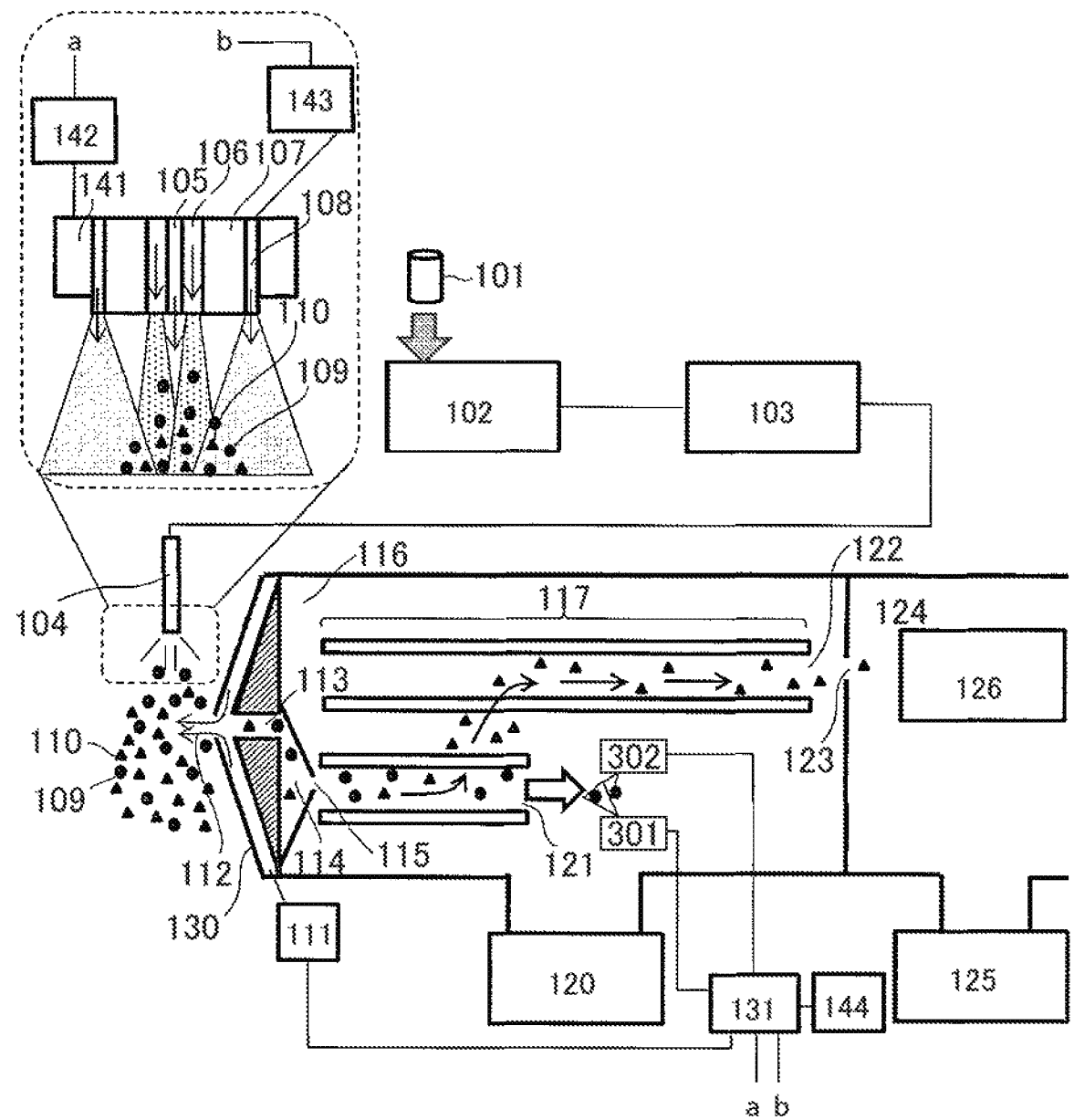
FIG. 7 is a schematic diagram illustrating example configuration of an ion analysis device.

FIG. 7 is a schematic diagram illustrating example configuration of an ion analysis device that uses light scattering to measure the charged droplets 109. The ion analysis device in accordance with the embodiment differs from the first embodiment in the configuration of the droplet measurement unit, and the rest of the configuration is the same as the first embodiment. Different points from the first embodiment are here described mainly.

A light source 301 and a photodetector 302 are placed as a droplet measurement unit on the axis of the droplet outlet 121 of the ion guide 117. The light source 301 and the photodetector 302 are placed in positions on which the charged droplets 109 ejected from the droplet outlet 121 do not impinge directly. The charged droplets 109 ejected from the droplet outlet 121 are irradiated with light emitted from the light source 301, and then the scattered light scattered by the charged droplets 109 is detected by the photodetector 302 such as a photomultiplier or the like. The photodetector 302 transmits, to the analysis control section 131, an output signal proportional to the amount of charged droplets 109.

Where the light scattering is used to measure droplets, non-charged droplets can be also detected. Where APCI or APPI is employed as the ionization technique used in the ion source, high voltage is not applied to the liquid-sample flow path 105, so that the sprayed liquid droplets become electrically neutral. Even if such an ionization technique is employed, the amount of droplets can be measured by use of light scattering to achieve a reduction in apparatus contamination through the control illustrated in FIG. 6. Further, a reduction in sensitivity due to contamination can be monitored during the sample measurement and the need of maintenance can be displayed for the user. In FIG. 6, similar control may be achieved by adopting the amount of scattered light representing the amount of droplets, instead of the current value of the charged droplets.

Third Embodiment

The embodiment illustrates example adjustment for apparatus parameters based on the current value of the droplets and the ionic strength. The apparatus illustrated in FIG. 1 is used as an ion analysis device. In the embodiment, the analysis control section 131 receives as input a signal from the ammeter 119 and also a signal indicating the analyte ion strength from the ion analysis unit 126 which is placed within the ion analysis chamber 124. And the analysis control section 131 reads the detected amount of droplets and the analyte ion strength to adjust the apparatus parameters.

Figure 8:
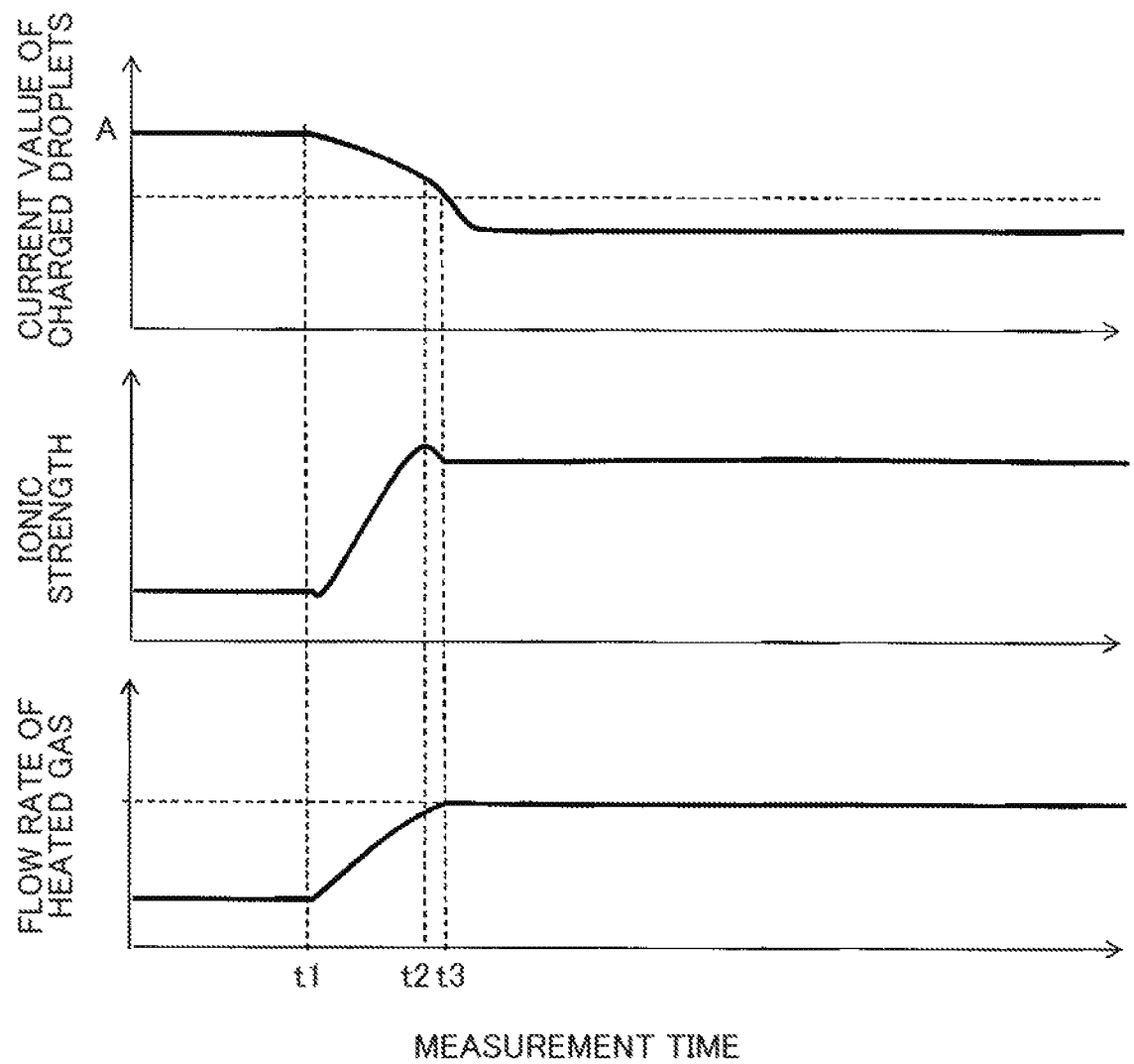
FIG. 8 is a diagram illustrating an example control sequence to control apparatus parameters.

FIG. 8 is a diagram illustrating an example control sequence to control apparatus parameters. FIG. 8 illustrates the control on the current value of the charged droplets, the analyte ion strength, and the flow rate of heated gas. Until time t1, the current value of the charged droplets exceeds the threshold A and therefore the apparatus is easily contaminated. Also, the ionic strength is low and therefore the sensitivity is low. At time t1, the analysis control section 131 instructs the flow-rate control section 143 to increase the flow rate of heated gas, whereupon the charged droplets volatilize, resulting in a decrease of the current value. On the other hand, enhancement in volatilization enhances the ionization efficiency to increase the ionic strength. At time t2, the maximum ionic strength is reached, but the current value of the charged droplets still exceeds the threshold A. The flow-rate control section 143 further increases the flow rate of heated gas, whereupon the current value of the charged droplets decreases and the ionic strength decreases due to thermal decomposition. To prevent the apparatus from being contaminated, the analysis control section 131 instructs the flow-rate control section 143 to increase the flow rate of heated gas until time t3 at which the current value of the charged droplets becomes at or below the threshold A, and then to maintain the flow rate after that. In the control in FIG. 8, the control on the flow rate of heated gas is illustrated as an example control on the apparatus parameters, but the temperature of the heated gas may be controlled.

Figure 9:
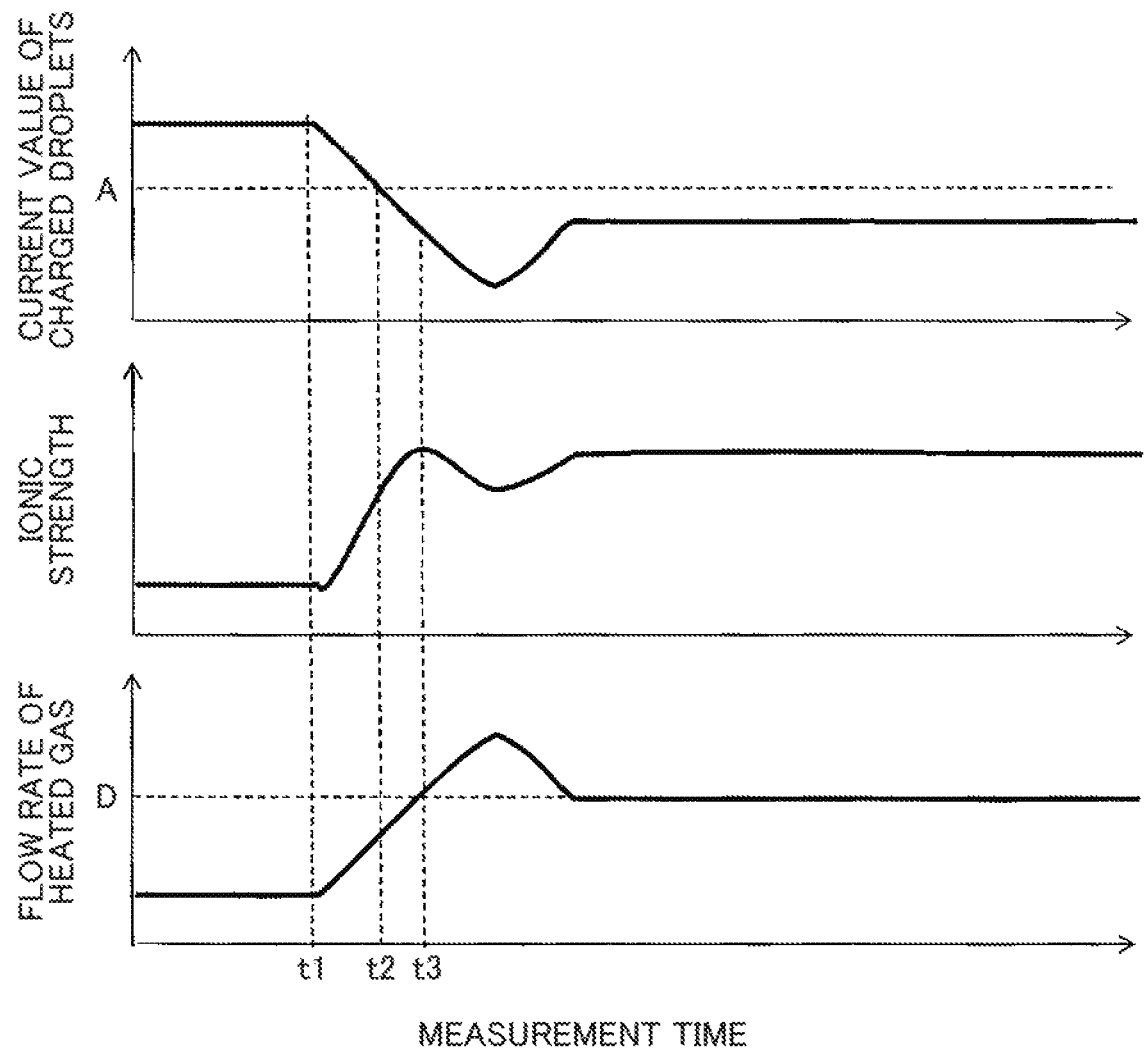
FIG. 9 is a diagram illustrating an example control sequence to control apparatus parameters.

FIG. 9 is a diagram illustrating another example control sequence to control the apparatus parameters. In this example, a control sequence is illustrated where after the current value of the charged droplets falls at or below the threshold, the ionic strength reaches its maximum value. Until time t1, the current value of the charged droplets exceeds the threshold A and therefore the apparatus is easily contaminated. Also, the ionic strength is low and therefore the sensitivity is low. At time t1, when the analysis control section 131 instructs the flow-rate control section 143 to increase the flow rate of heated gas, the charged droplets volatilize and therefore the current value is lowered. Also, the ionization efficiency is increased to increase the ionic strength of the analyte. At time t2, the current value of the charged droplets falls below the threshold A, and therefore the contamination in the apparatus is reduced. On the other hand, the ionic strength tends to increase. If the flow rate of heated gas is further increased, there is a possibility of further increase in sensitivity. Accordingly, increasing the flow rate of heated gas is continued, so that the ionic strength increases until time t3. As the flow rate of heated gas is further increased, the ionic strength is reduced due to thermal decomposition of the sample. For adjusting the flow rate of heated gas to meet the condition for providing maximum sensitivity, the analysis control section 131 instructs the flow-rate control section 143 to decrease the flow rate to the same value as that of the flow rate of heated gas D at time t3.

The control sequences illustrated in FIG. 8 and FIG. 9 enable the adjustment for the conditions for low contamination and high sensitivity, and therefore the user's time to adjust the parameters can be reduced. It is noted that, in the case of using the apparatus illustrated in the second embodiment as the ion analysis device, similar control can be performed by replacing the current value of the charged droplets illustrated in FIG. 8 or FIG. 9 with the amount of scattered light representing the amount of droplets.

Fourth Embodiment

The following description is of an example control sequence for an ion analysis device using LC. The apparatus illustrated in FIG. 1 was used as an ion analysis device.

In LC, in order to determine the separation conditions, the solvent composition is varied to measure the analyte ions 110. The volatilization efficiency of the solvent in the charged droplets 109 varies depending on solvent composition. Therefore, there is a need to search for conditions to attain sufficient sensitivity by adjusting apparatus parameters such as the temperature of the ion source, the flow rate of heated gas, and/or the like, in accordance with the solvent composition. Typically, the LC separation time is about 10 minutes and the time required for detecting an analyte is several seconds. In the case of using LC, because the time during detection of an analyte is short, there is, typically, a need to measure samples over several times in order to adjust the apparatus conditions such as the flow rate of heated gas, temperatures and/or the like. Because the separation time is consumed for each sample measurement, using LC suffers from the disadvantage of time-consuming condition adjustment. In the embodiment, a control sequence is described in which the apparatus parameters are adjusted by use of the current value of the charged droplets before the analyte is detected, in order to adjust the apparatus conditions in a short time.

Figure 10:
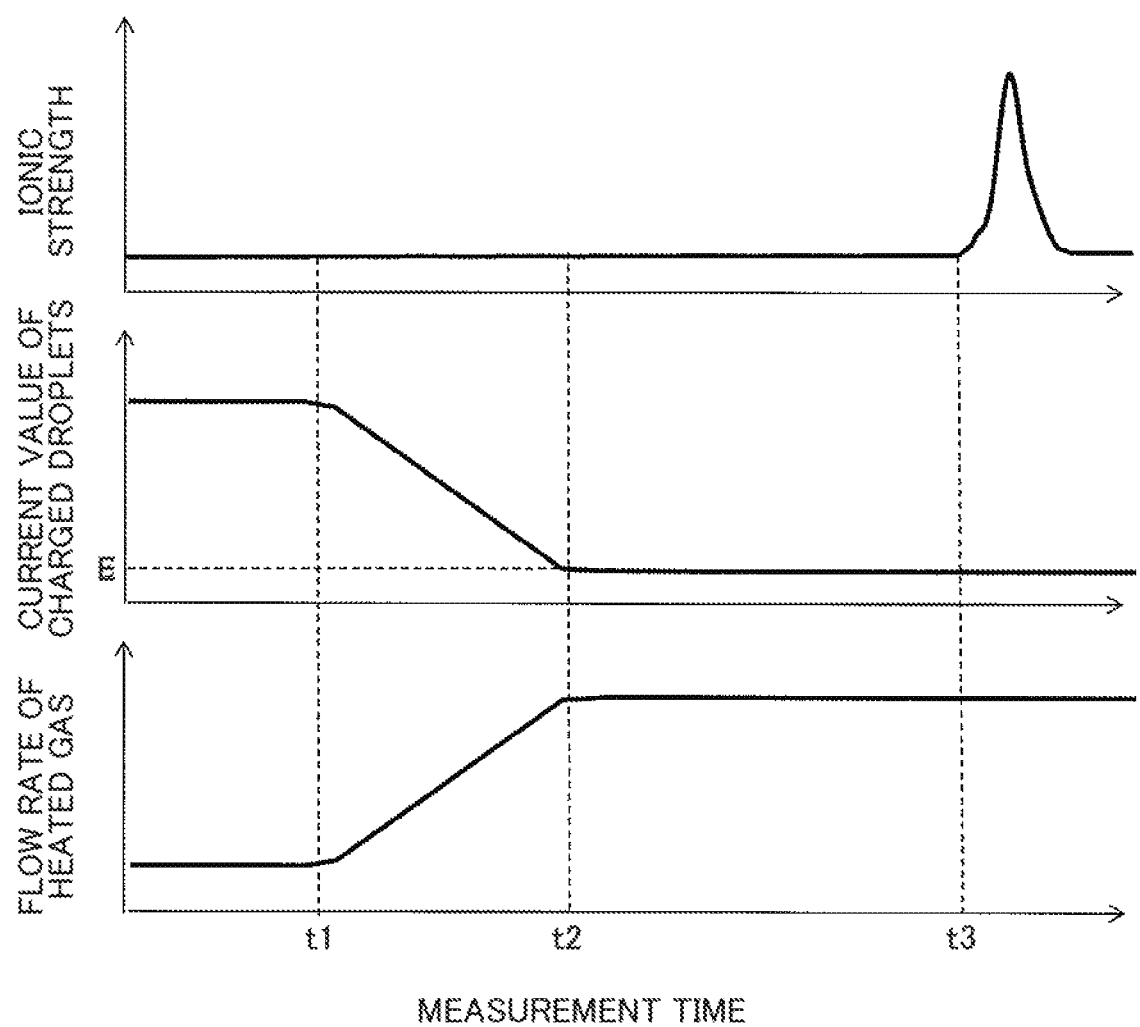
FIG. 10 is a diagram illustrating an example control sequence where LC is used.

FIG. 10 is a diagram illustrating an example control sequence in the case of using LC. Until time t3, the analyte is retained in LC, and no analyte ion 110 is detected. However, the LC solvent flows continuously, so that the charged droplets 109 and ions other than the analyte are produced. In the case of an embodiment illustrated in FIG. 10, at the beginning, the flow rate of heated gas is low and the current value of the charged droplets is high. At time t1, in response to an instruction from the analysis control section 131, the flow-rate control section 143 increases the flow rate of heated gas, whereupon the solvent volatilizes and therefore the current value of the charged droplets decreases. In ESI, if the charged droplets volatilize sufficiently, the amount of produced ions increases, resulting in higher sensitivity.

A threshold E of the current value of the charged droplets required to attain sufficient sensitivity is previously set as illustrated in FIG. 10. The analysis control section 131 completes the adjustment for the apparatus parameter, that is, the adjustment of the flow rate of heated gas, at time t2 when the current value of the charged droplets decreases to the threshold E. By this control sequence, the apparatus conditions can be adjusted to suit the solvent composition before the detection of analyte ions, so that the user's time to adjust the apparatus parameters can be saved. Also, high-sensitive measurement of analytes can be provided independently of solvent compositions. The embodiment is effective in any other ion sources than ESI as long as they spray and provide a liquid sample. For example, APCI, APPI or the like may be used instead of ESI. In the case where APCI or APPI in which droplets are not electrically charged is used as an ion source, the amount of droplets may be measured by use of light scattering as described in the second embodiment, or the like.

It should be noted that the present invention is not limited to the above embodiments and encompasses numerous modifications. For example, the above embodiments have been described in detail for the purpose of explaining the present invention clearly, and the present invention is not necessarily limited to including all the components and configurations described above. Further, part of the configuration in an embodiment may be substituted by configuration in another embodiment, and configuration in an embodiment may be added to configuration in another embodiment. Further, part of the configuration in each embodiment may be added to, removed from or substituted by anther configuration.

LIST OF REFERENCE SIGNS

101 . . . Liquid sample
102 . . . Sample Pretreatment device
103 . . . Liquid chromatograph device
104 . . . ESI spray
109 . . . Charged droplets
110 . . . Analyte ions
111 . . . Gas feeding control section
112 . . . Counter gas
117 . . . Ion guide
118 . . . Electrode
119 . . . Ammeter
121 . . . Charged droplet outlet
122 . . . Ion outlet
124 . . . Ion analysis chamber
126 . . . Ion analysis unit
130 . . . Counter plate electrode
131 . . . Analysis control section
141 . . . Heater
142 . . . Temperature control section
143 . . . Flow-rate control section
144 . . . Display unit
301 . . . Light source
302 . . . Photodetector

The invention claimed is:

1. An ion analysis device, comprising:
an ion source that ionizes an analyte in a liquid sample;
an ion guide into which droplets and ions produced in the ion source are introduced, the ion guide having different outlets, one outlet being an ion outlet for the ions and the other outlet being a droplet outlet for the droplets;
an ion analysis unit that analyzes ions ejected from the ion outlet;
a droplet measurement unit that is placed on an axis of the droplet outlet, and that measures the amount of droplets; and
an analysis control section that compares the amount of droplets measured at the droplet measurement unit with a threshold.

2. The ion analysis device according to claim 1, wherein the ion analysis unit is anyone of a mass analyzer, an ion mobility spectrometer, and a differential mobility spectrometer.

3. The ion analysis device according to claim 1, wherein the ion source is an ion source using any one of Electrospray ionization, Atmospheric pressure chemical ionization, and Atmospheric pressure photoionization.

4. The ion analysis device according to claim 1, wherein the droplets are charged droplets and the droplet measurement unit includes an ammeter.

5. The ion analysis device according to claim 1, wherein the droplet measurement unit includes a light source and a photodetector, and the droplet measurement unit applies light from the light source to the droplets, and detects scattered light from the droplets at the photodetector.

6. The ion analysis device according to claim 1, wherein if the amount of droplets is equal to or below the threshold, the analysis control section performs any one processing of giving a warning, stopping a sample measurement, or suspending the subsequent sample measurement.

7. The ion analysis device according to claim 1, wherein an ionic strength of an analyte and the amount of droplets are measured during a sample measurement.

8. An ion analysis device, comprising:
an ion source that ionizes an analyte in a liquid sample;
an ion guide into which droplets and ions produced in the ion source are introduced, the ion guide having different outlets, one outlet being an ion outlet for the ions and the other outlet being a droplet outlet for the droplets;
an ion analysis unit that analyzes ions ejected from the ion outlet;
a droplet measurement unit that is placed on an axis of the droplet outlet, and that measures the amount of droplets; and an analysis control section into which a signal is input from the droplet measurement unit, wherein the analysis control section adjusts apparatus parameters on the basis of the amount of droplets measured at the droplet measurement unit.

9. The ion analysis device according to claim 8, wherein the apparatus parameters include a flow rate of counter gas directed outward from an ion inlet of the ion guide, a temperature of the ion source, and a flow rate of heated gas passed through the ion source.

10. The ion analysis device according to claim 8, further comprising a liquid chromatograph device, wherein the analysis control section adjusts the apparatus parameters on the basis of an amount of droplets measured at the droplet measurement unit during a retention time in which an analyte is not detected.

11. An ion analysis device, comprising:

an ion source that ionizes an analyte in a liquid sample;

an ion guide into which droplets and ions produced in the ion source are introduced, the ion guide having different outlets, one outlet being an ion outlet for the ions and the other outlet being a droplet outlet for the droplets;

an ion analysis unit that analyzes ions ejected from the ion outlet;

a droplet measurement unit that is placed on an axis of the droplet outlet, and that measures the amount of droplets; and an analysis control section that receives, as input, a signal indicating an analyte ion strength from the ion analysis unit, and a signal indicating the amount of droplets from the droplet measurement unit, wherein the analysis control section adjusts apparatus parameters on the basis of the analyte ion strength and the amount of droplets.

12. The ion analysis device according to claim 11, further comprising a liquid chromatograph device.

13. The ion analysis device according to claim 11, wherein the analysis control section adjusts the apparatus parameters such that the analyte ion strength reaches its maximum under conditions that the amount of droplets becomes equal to or below a threshold.

* * * * *